(12) United States Patent
Bashir-Hashemi

(10) Patent No.: US 6,222,068 B1
(45) Date of Patent: Apr. 24, 2001

(54) NITROCUBANES

(75) Inventor: Abdollah Bashir-Hashemi, Bridgewater, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 08/228,245

(22) Filed: Apr. 14, 1994

Related U.S. Application Data

(63) Continuation of application No. 07/955,386, filed on Oct. 1, 1992, now abandoned.

(51) Int. Cl.⁷ ..................................................... C07C 61/12

(52) U.S. Cl. ............................................................. 562/498
(58) Field of Search ............................................. 562/498

(56) References Cited

U.S. PATENT DOCUMENTS 3,418,368 * 12/1968 Dunn ..................................... 562/498
3,517,055 * 6/1970 Loeffler ................................ 562/498
3,558,704 * 1/1971 Gregory ................................ 562/498

* cited by examiner

*Primary Examiner*—Michael L. Shippen
(74) *Attorney, Agent, or Firm*—John F. Moran

(57) ABSTRACT

An efficient direct functionalization of nitrocubanes has been achieved by irradiation of a solution in an oxalyl halide to yield halogenated and halocarbonylated derivatives of nitrocubanes.

1 Claim, No Drawings

NITROCUBANES

This application is a continuation of application Ser. No. 07/955,386, filed Oct. 1, 1992, now abandoned.

GOVERNMENTAL INTEREST

The Government has rights in this invention pursuant to Contract No. DAAA21-89-C-0013 awarded by the U.S. Army.

The invention described herein was made under a contract with the Government and may be used and licensed by or for the Government.

FIELD OF USE

This invention describes the direct functionalization of nitrocubanes via irradiation in the presence of an oxalyl halide.

BACKGROUND OF THE INVENTION

Considerable effort in recent years has been directed toward the synthesis of polynitrocubanes because of the potential use of this class of energetic materials as explosives, propellants, fuels and binders (Chemistry of Energetic Materials; Ed., G. A. Olah; D. R. Squire; Academic Press, Inc., San Diego, Calif., 1991. Also see Carbocyclic Cage Compounds; Ed., E. J. Osawa; O. Yonemitsu; VCH Publishers, Inc., New York, N.Y., 1992). The compact structures of cage molecules result in high densities, and the introduction of $NO_2$ groups further enhances the density. The strain energy present in the cubane skeleton (>166 kcal/mol) is an added bonus to its performance. Furthermore, preliminary results with polynitrocubanes indicate that such compounds are thermally very stable and are also very insensitive energetic materials. Consequently, it is of interest to introduce functional groups on the cubane skeleton which can be converted to nitro group or other active functionalities.

Direct functionaliztion of nitrocubanes, while an attractive approach, has not heretofore been realized. Cationic or anionic reactions, due to the activity of the nitro groups give either decomposed products or recovered starting materials. We report here an efficient direct functionalization of a nitrocubane molecule by its irradiation in a solution of oxalyl halide (for a related case see Wiberg, K. B.; 10$^{th}$ Annual Working Group Meeting, Jun. 3–6, 1992, Kiamesha Lake, N.Y. For much simpler cases see Wiberg, K. B.; Williams, Jr., V. Z.; J. Org. Chem., 1970, 35, 369; Applequist, D. E.; Saski, T.; J. Org. Chem.; 1978, 43, 2399). This new and potentially powerful synthetic development will greatly shorten the number of steps necessary to obtain nitrocubane derivatives which are otherwise difficult to synthesize.

SUMMARY OF THE INVENTION

A solution of 1,4-dinitrocubane (Eaton, P. E.; et al; J. Org. Chem.; 1984, 49, 185; Eaton, P. E.; Wicks, G. E.; J. Org. Chem.; 1988, 53, 5353) in oxalyl chloride was irradiated under a sunlamp for 12 h at room temperature. After removing oxalyl chloride under reduced pressure, the reaction mixture was hydrolyzed and partioned between ethyl acetate and 5% aqueous NaOH. From the organic phase was isolated 2-chloro-1,4-dinitrocubane, 3, and 2,5-dichloro-1,4-dinitrocubane, 4. After acidification of the alkaline layer with HCl and extraction with ethyl acetate, 2-carboxy-1,4-dinitrocubane, 5, was obtained in 68% yield.

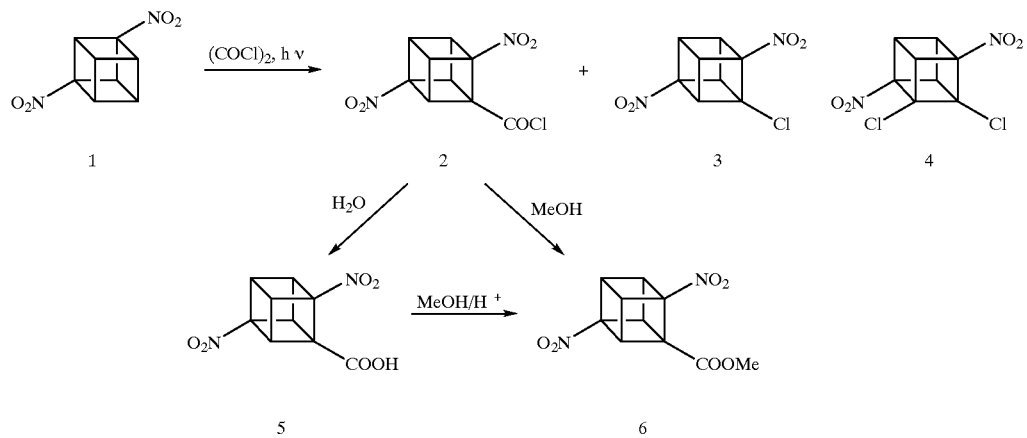

The structures of 3, 4, and 5 were confirmed by NMR spectrometry. Furthermore, Compound 5 was converted to the corresponding 2-carbomethoxy-1,4-dinitrocubane 6 by esterification using MeOH, and the molecular structure of 6 was confirmed by X-ray crystallographic analysis.

DESCRIPTION OF THE PREFERRED EMBODIMENTS

The following section describes specific experimental procedures used for the synthesis:

A mixture of 1,4-dinitrocubane, 1, (388 mg, 2.0 mmol) in oxalyl chloride (50 mL) was photolyzed under a sunlamp for 18 h at room temperature. Oxalyl chloride was removed on a rotary evaporator and the solid residue was partioned between EtOAc (40 mL) and NaOH solution (5%, 30 mL). After stirring for 3 h, the organic phase was separated, washed with brine, dried over anhydrous $Na_2SO_4$ and concentrated under reduced pressure. The residue was chromatogrphed on silica gel using hexane/$CH_2Cl_2$ (1:1) to give 2-chloro-1,4-dinitrocubane 3, m.p. 145–147° C.; $^1$H NMR ($CDCl_3$); δ 4.84 (m, 2H); 4.71 (m, 3H); and 2,5-dichloro-1,4-dinitrocubane, 4, m.p. 188–190° C.; $^1$H NMR ($CDCl_3$); δ 4.90 (dd, 2H); 4.78 (dd, 2H).

The alkaline layer was acidified with HCl (10%) and organic materials were extracted with EtOAc (2×30 mL). The organic phase was washed with bring, dried over Na$_2$SO$_4$, and concentrated via rotary evaporator to give 400 mg or a crude product which was triturated with hexane/acetone 10:1, (5.0 mL) to give 2-carboxy-1,4-dinitrocubane, 5, m.p. 187–189 (Dec) ° C.; $^1$H NMR (acetone-d$_6$); δ 4.96 (m, 2H); 4.74 (m, 3H).

Compound 5 (100 mg, 0.4 mmol) was stirred with MeOH (20 mL) and MeSO$_3$H (4 drops) at reflux overnight. The reaction mixture was concentrated and then dissolved in ethyl acetate (20 mL). The solution was washed with aqueous Na$_2$CO$_3$ (5%), then brine, dried over anhydrous Na$_2$SO$_4$ and concentrated. The residue was triturated with ether hexane (1:1) to give 2-carbomethoxy-1,4-dinitrocubane 6 m.p.=165° C.; $^1$H NMR (CDCl$_3$), δ 4.92 (M, 2H); 4.62 (m, 3H), 3.80 (s, 3H).

In another expremint, the solid residue from the reaction of 1,4-dinitrocubane (100 mg) and oxalyl chloride (20 mL) under a sunlamp (vide supra) was treated with methanol (20 mL) for 4 h at room temperature. The excess methanol was evaporated and the residue was dissolved in ethyl acetate (20 mL). The organic layer was washed with 5% aqueous Na$_2$CO$_3$ and then brine. After drying over Na$_2$SO$_4$ and then concentration, the crude product was chromatographed on silica gel using hexane/CH$_2$Cl$_2$ (1:1) to give compounds 3, 4, and 6.

What is claimed is:

1. 2-carboxy-1,4-dinitrocubane

* * * * *